US010472299B2

(12) United States Patent
Matzger et al.

(10) Patent No.: US 10,472,299 B2
(45) Date of Patent: Nov. 12, 2019

(54) EXPLOSIVE MICROPOROUS COORDINATION POLYMERS

(71) Applicant: The Regents of the University of Michigan, Ann Arbor, MI (US)

(72) Inventors: Adam J. Matzger, Ann Arbor, MI (US); Kyle McDonald, Kissimmee, FL (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 208 days.

(21) Appl. No.: 15/631,519

(22) Filed: Jun. 23, 2017

(65) Prior Publication Data

US 2017/0369387 A1 Dec. 28, 2017

Related U.S. Application Data

(60) Provisional application No. 62/354,298, filed on Jun. 24, 2016.

(51) Int. Cl.
| | |
|---|---|
| C06B 25/00 | (2006.01) |
| C06B 21/00 | (2006.01) |
| C07F 3/06 | (2006.01) |
| C06B 45/00 | (2006.01) |
| C06B 45/04 | (2006.01) |
| D03D 23/00 | (2006.01) |
| D03D 43/00 | (2006.01) |

(52) U.S. Cl.
CPC .......... *C06B 25/00* (2013.01); *C06B 21/0083* (2013.01); *C07F 3/06* (2013.01)

(58) Field of Classification Search
USPC ........................ 149/2, 17, 88, 108.8, 109.4
See application file for complete search history.

(56) References Cited

U.S. PATENT DOCUMENTS

| | | | |
|---|---|---|---|
| 5,648,508 A | 7/1997 | Yaghi | |
| 6,929,679 B2 | 8/2005 | Muller et al. | |
| 6,930,193 B2 | 8/2005 | Yaghi et al. | |
| 7,196,210 B2 | 3/2007 | Yaghi et al. | |
| 7,202,385 B2 | 4/2007 | Mueller et al. | |
| 8,197,619 B1* | 6/2012 | Nelson | C06B 43/00 149/105 |
| 8,257,519 B1* | 9/2012 | Nelson | C06B 43/00 149/1 |
| 8,425,659 B2 | 4/2013 | Matzger et al. | |

(Continued)

OTHER PUBLICATIONS

Park, Kyo Sung, et al.: "Exceptional chemical and thermal stability of zeolitic imidazolate frameworks," Proceedings of the National Academy of Sciences, vol. 103, No. 27, Jul. 5, 2006, pp. 10186-10191.

*Primary Examiner* — James E McDonough
(74) *Attorney, Agent, or Firm* — Harness, Dickey & Pierce, P.L.C.

(57) ABSTRACT

Employing non-energetic MCPs as hosts (fuel) for the adsorption of oxidant molecules enables the intimate and molecular scale mixing of fuel and oxidizer on a level that is not commonly achievable in traditional energetic mixtures. The adsorption of the oxidants into MOF-5 resulted in increased heat released upon decomposition, which shows potential for utilization of this method as a platform to develop high-performance primary energetic materials.

15 Claims, 16 Drawing Sheets

(56) References Cited

U.S. PATENT DOCUMENTS

| | | | |
|---|---|---|---|
| 8,506,734 B1 * | 8/2013 | Nelson | C06B 43/00 149/109.2 |
| 9,096,530 B2 | 8/2015 | Matzger et al. | |
| 9,353,129 B2 | 5/2016 | Matzger et al. | |
| 2005/0154222 A1 | 7/2005 | Muller et al. | |
| 2005/0192175 A1 | 9/2005 | Yaghi et al. | |
| 2006/0154807 A1 | 7/2006 | Yaghi et al. | |
| 2006/0185388 A1 | 8/2006 | Muller et al. | |
| 2006/0252641 A1 | 11/2006 | Yaghi et al. | |
| 2007/0068389 A1 | 3/2007 | Yaghi | |
| 2011/0021341 A1 | 1/2011 | Matzger et al. | |
| 2013/0305922 A1 | 11/2013 | Matzger et al. | |
| 2014/0179514 A1 | 6/2014 | Matzger et al. | |

* cited by examiner

EXPLOSIVE MICROPOROUS COORDINATION POLYMERS

CROSS-REFERENCE TO RELATED APPLICATIONS

This application claims the benefit of U.S. Provisional Application No. 62/354298, filed Jun. 24, 2016. The entire disclosure of the above application is incorporated herein by reference.

GOVERNMENT SUPPORT

This invention was made with government support under Grant No. HDTRA1-15-1-001 awarded by the Defense Threat Reduction Agency (DTRA). The Government has certain rights in this invention.

INTRODUCTION

Explosives, and related energetic materials such as propellants and pyrotechnics, have a large amount of stored chemical energy that can be released with a suitable initiation event. The rapid release is facilitated by the proximity of fuel and oxidizer within the molecule. The prototypical energetic material 2,4,6-trinitrotoluene (TNT) consists of oxidizing nitro groups attached to an aromatic ring providing fuel in the form of carbon and hydrogen atoms. TNT, like the vast majority of explosives, is under-oxidized meaning that it lacks sufficient oxidizing power for the amount of fuel present. Such a situation leads to reduction of performance and has motivated the development of more "oxygen balanced" materials although the limitations of scalable chemical synthesis have proven difficult to overcome thus far, and therefore under-oxidized energetic materials are currently the state of the art.

Oxygen balance (OB %) describes the amount of oxygen present in the material compared to that needed for complete conversion of carbon in the material to $CO_2$, nitrogen to $N_2$, and oxygen to water. An alternative strategy to chemical synthesis of oxygen-balanced energetics is to use physical mixtures of oxidants with fuel-rich molecules; however, the need for intimate contact between reactants typically handicaps this approach. Achieving molecular scale mixing of components can be accomplished by co-crystallization under certain conditions.

In U.S. Pat. No. 8,506,734, host guest complexes have guest energetic molecules in the pores of metal-organic frameworks. The compositions are intended for insensitive munitions (IM) compliant weapons systems, and as such they exhibit decreased sensitivity to shock and other detonation conditions than the individual guest energetic material.

SUMMARY

Guest host complexes are provided that offer advantageous properties as energetic materials or explosives. Individual molecules of energetic materials are infiltrated into the pores of a nanostructured sorbent. The structures are characterized by high levels of occupancy in the pores and a general absence of competition for occupancy by solvent molecules. As a result of the composition and/or the method of synthesis, the host guest complex containing the energetic material is observed to be more sensitive to shock than the energetic material itself.

It has also been discovered that complexes with good (near zero) oxygen balance can be prepared by infiltrating energetic materials having a positive oxygen balance (OB %) into the pores. Advantageously, the materials exhibit higher detonation pressure and velocity when the OB % is close to zero.

DRAWINGS

The drawings described herein are for illustration purposes only and are not intended to limit the scope of the present disclosure in any way.

Figure 3:
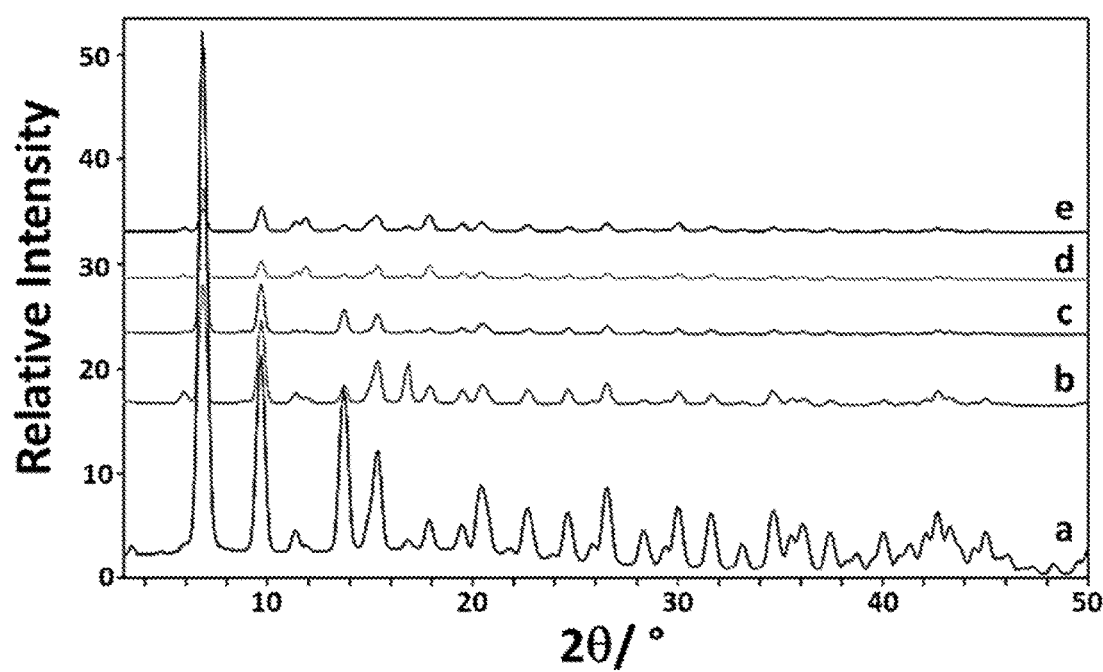

FIG. 3 shows Powder X-Ray diffraction patterns collected to monitor the structural integrity of MOF-5 as a function of TNM loading—As synthesized MOF-5 (bottom curve a), MOF-5-TNM after 30 minutes (curve b), MOF-5-TNM after 1 hour (middle curve c), MOF-5-TNM after 3 hours (curve d), and MOF-5-TNM after 24 hours (top curve e).

Figure 4:
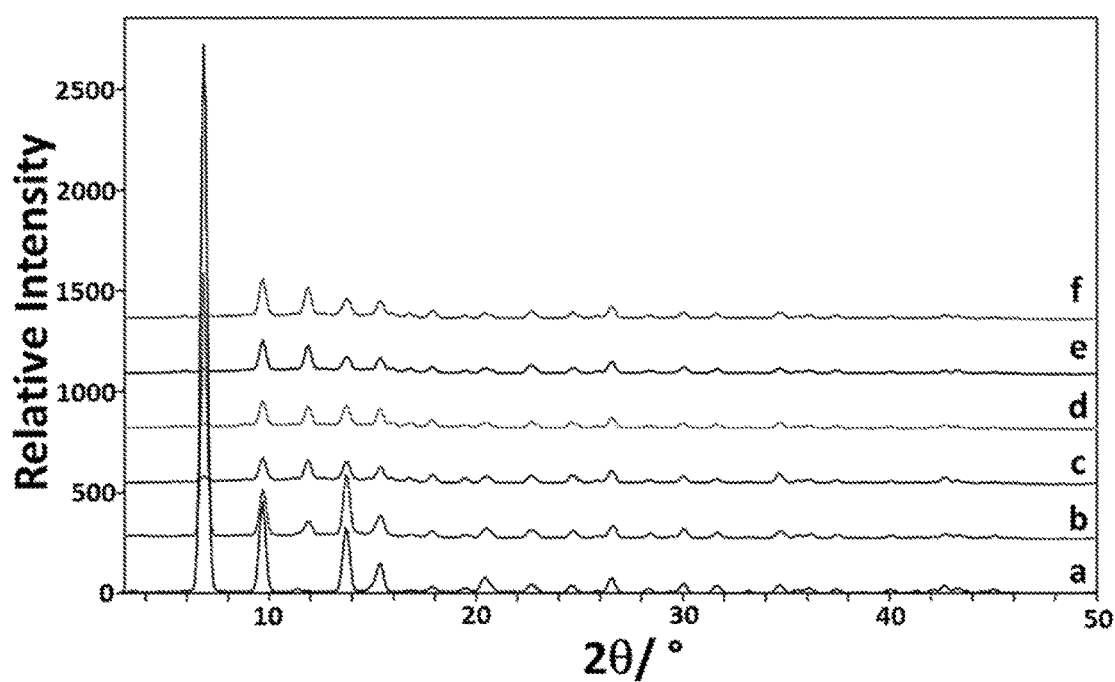

FIG. 4 shows Powder X-Ray diffraction patterns collected to monitor the structural integrity of MOF-5 as a function of HNE loading at 0.048 torr—As synthesized MOF-5 (bottom curve a), MOF-5-HNE after 5 minutes (curve b), MOF-5-HNE after 10 minutes (curve c), MOF-5-HNE after 15 minutes (curve d), MOF-5-HNE after 30 minutes (curve e), and MOF-5-HNE after 1 hour top curve f).

Figure 5:
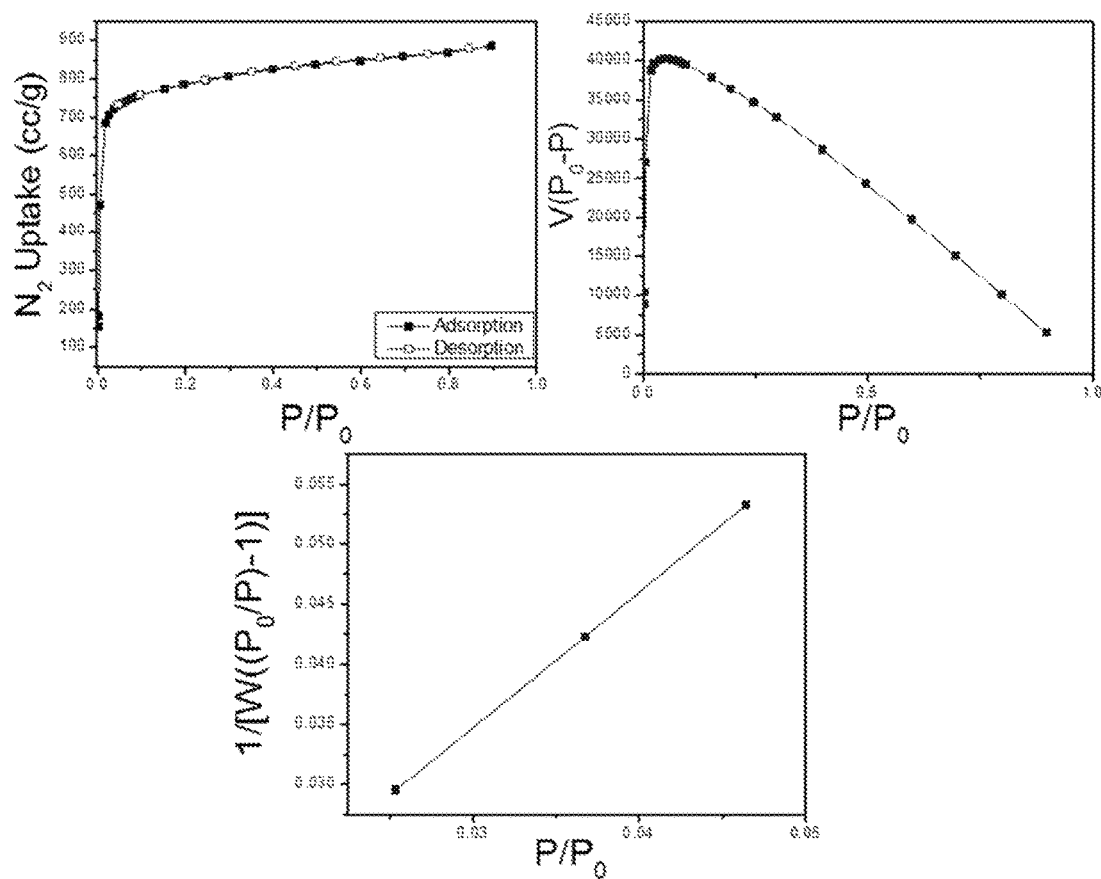

FIG. 5 shows (left) Nitrogen sorption isotherm collected on MOF-5, (middle) Consistency criterion plot for determining the $P/P_o$ range for BET analysis, and (right) BET plot used to calculate the surface area of MOF-5 (3087 $m^2g^{-1}$).

Figure 6:
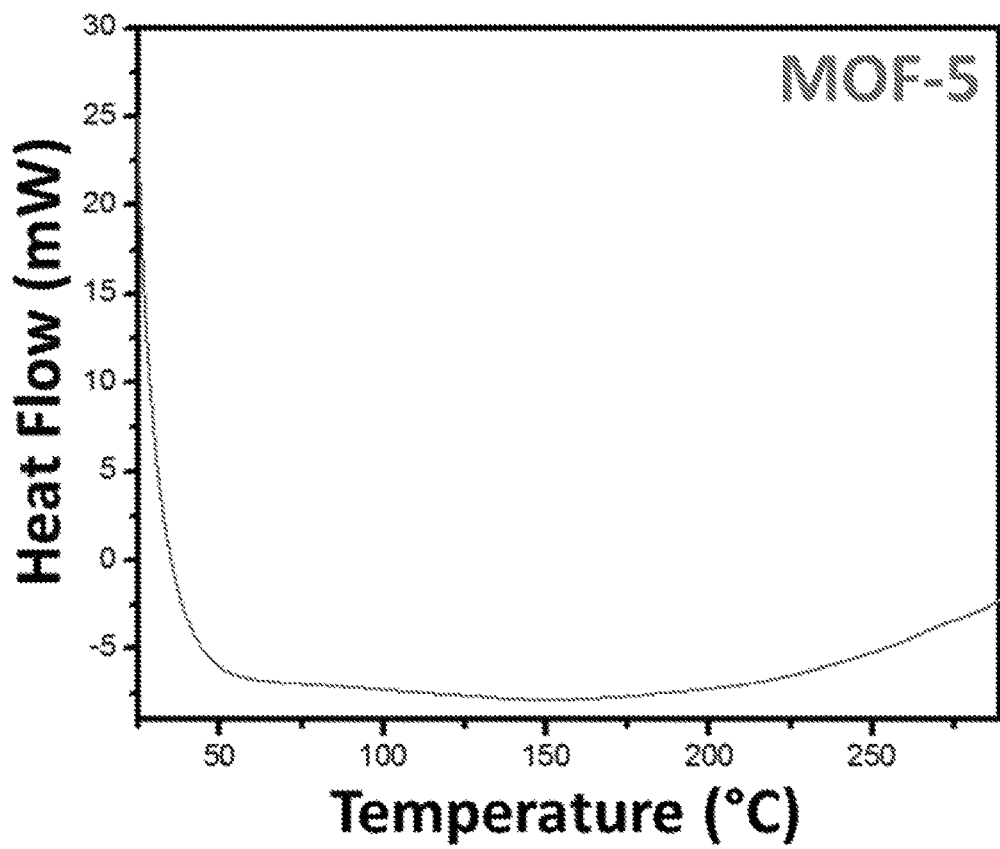

FIG. 6 is a graph showing DSC thermogram of MOF-5 at 20° C. $min^{-1}$ in the high-pressure pans.

Figure 7:
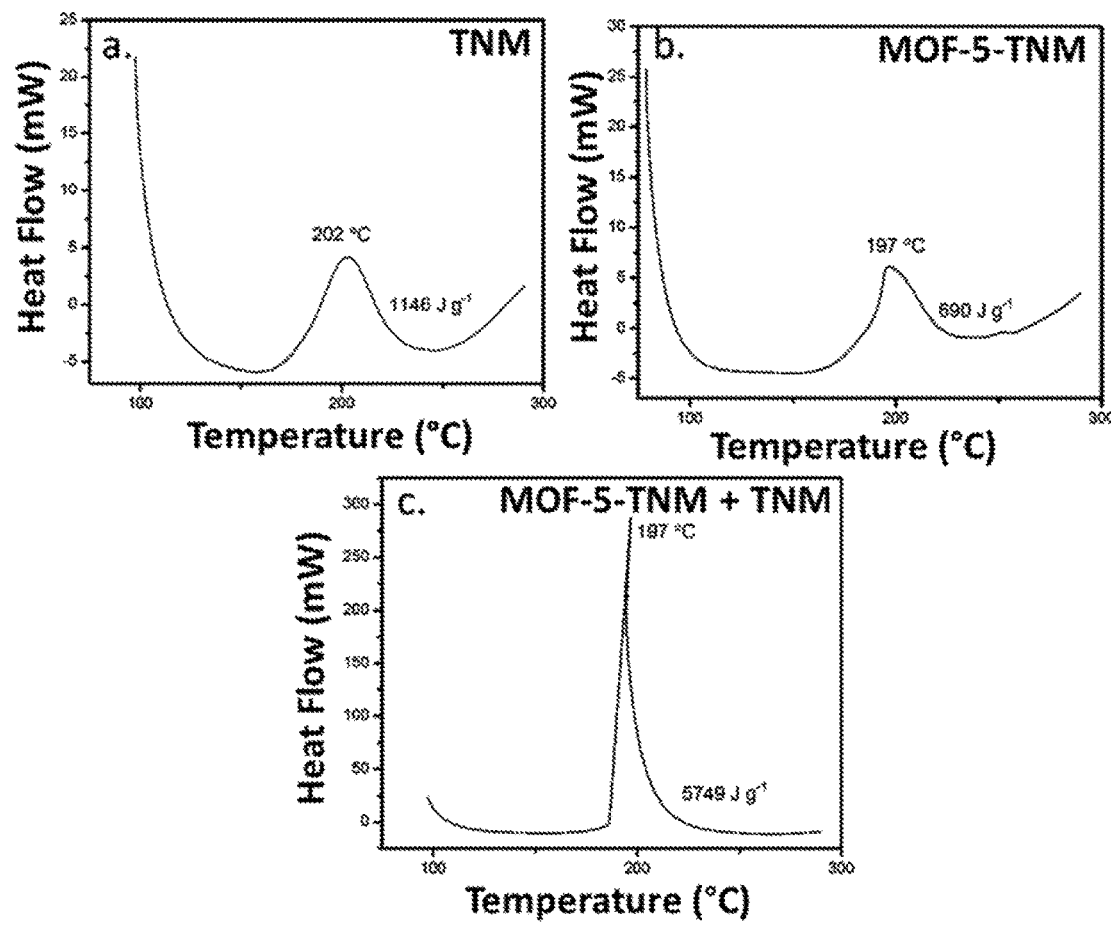

FIG. 7 are graphs showing DSC thermograms of a.) TNM (0.754 mg), b.) MOF-5-TNM (1.01 mg), and c.) MOF-5-TNM (0.650 mg) with excess TNM (0.786 mg) at 20° C. $min^{-1}$ in the high-pressure pans.

Figure 8:
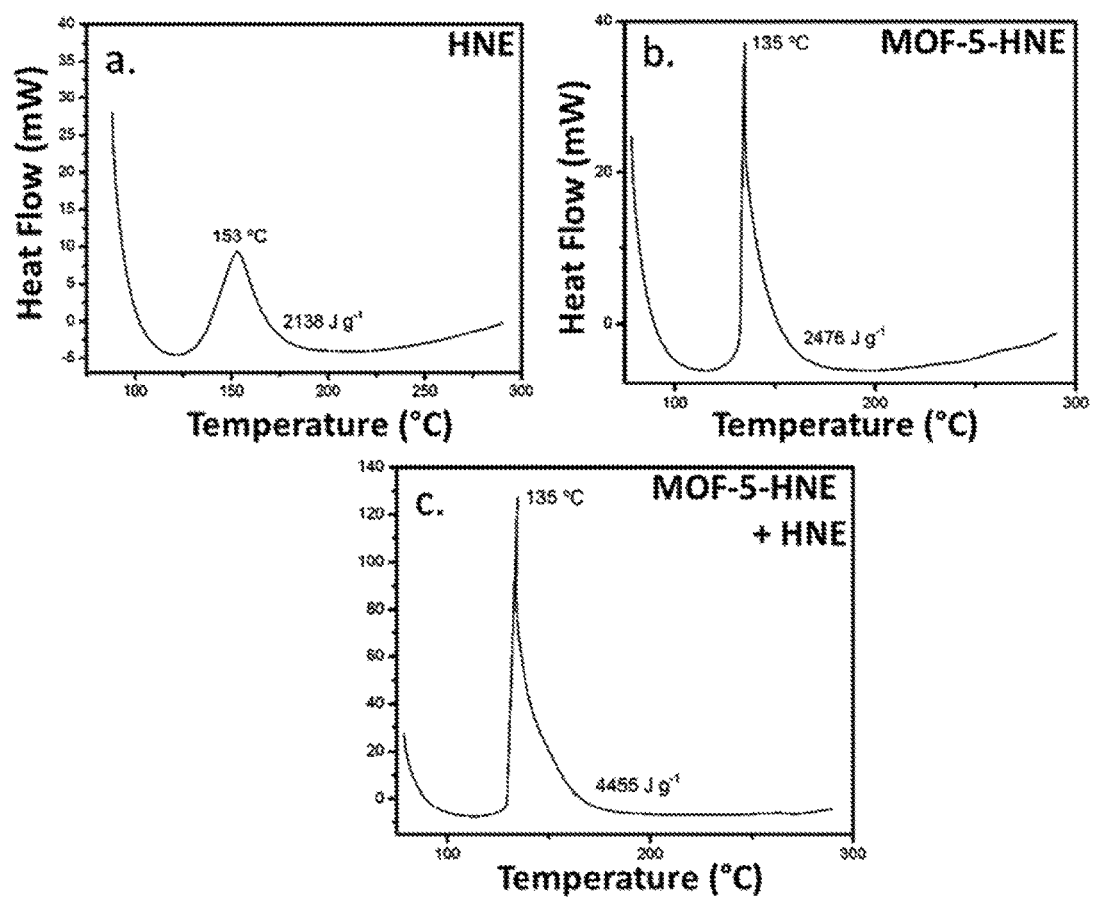

FIG. 8 are graphs showing DSC thermograms of a.) HNE (0.460 mg), b.) MOF-5-HNE (0.460 mg), and c.) MOF-5-HNE (0.426 mg) with excess HNE (0.514 mg) at 20° C. $min^{-1}$ in the high-pressure pans.

Figure 9:
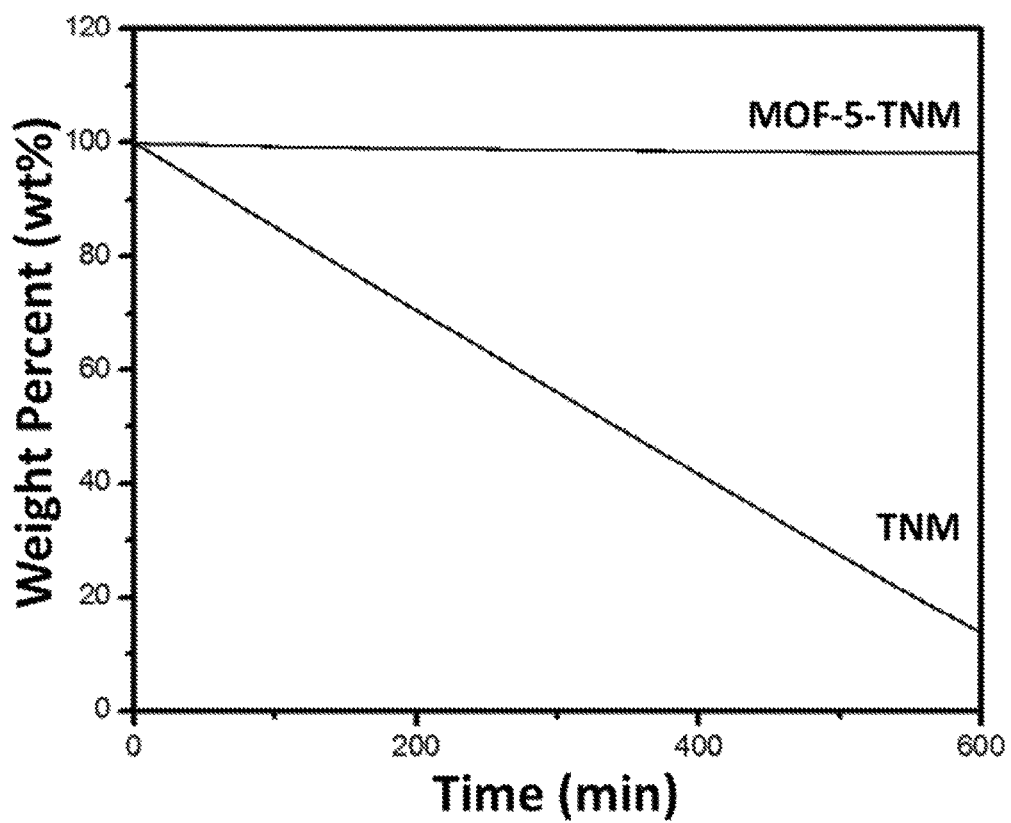

FIG. 9 is a graph showing a plot of the weight percent loss as a function of time for TNM (bottom line) and MOF-5-TNM (top line).

Figure 10:
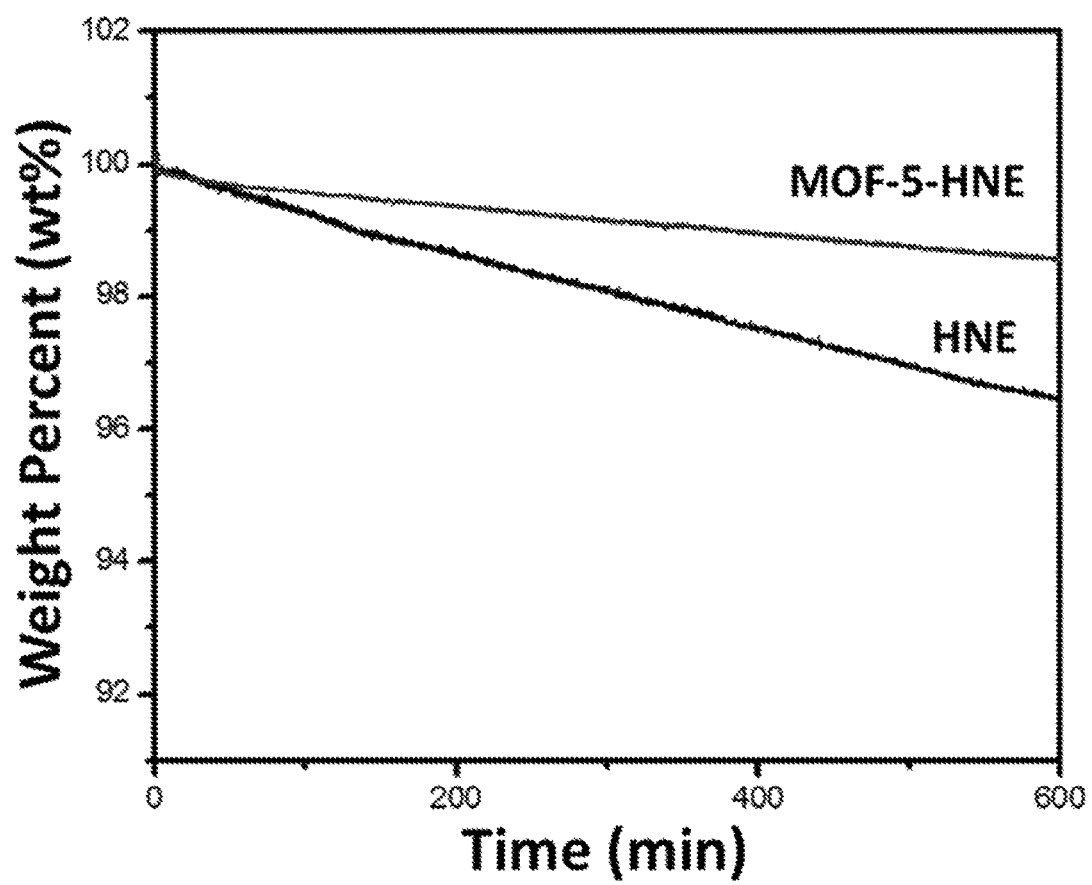

FIG. 10 is a graph showing a plot of the weight percent loss as a function of time for HNE (bottom line) and MOF-5-HNE (top line).

Figure 11:
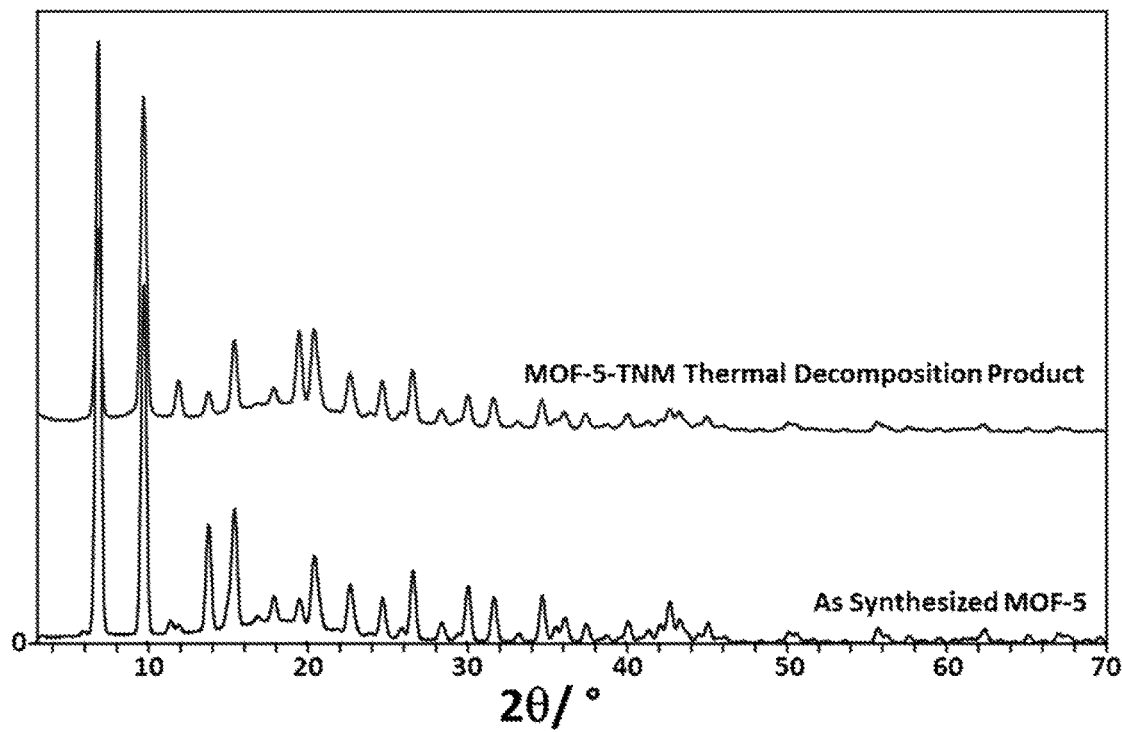

FIG. 11 is a graph showing PXRD of as synthesized MOF-5 (lower spectrum) and the thermal decomposition product of MOF-5-TNM (upper spectrum) showing a retention of the crystal structure after thermal initiation.

Figure 12:
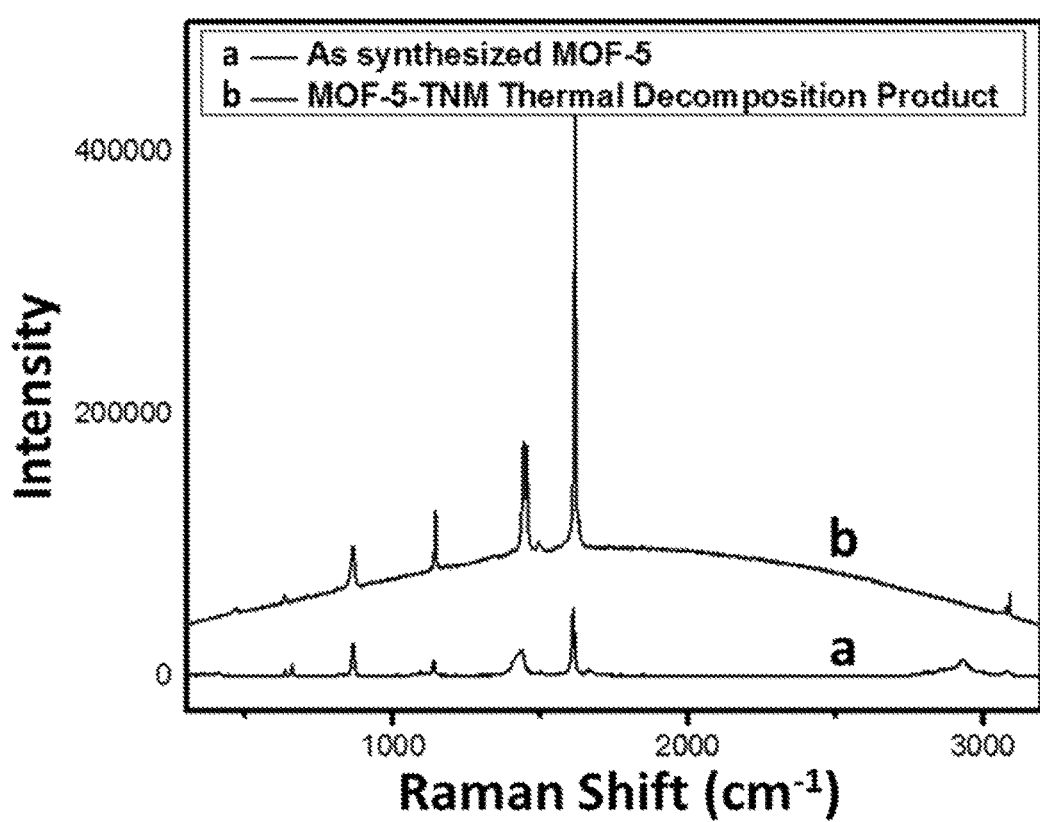

FIG. 12 is a graph showing Raman spectra of as synthesized MOF-5 (lower curve) and the thermal decomposition product of MOF-5-TNM (upper curve).

Figure 13:
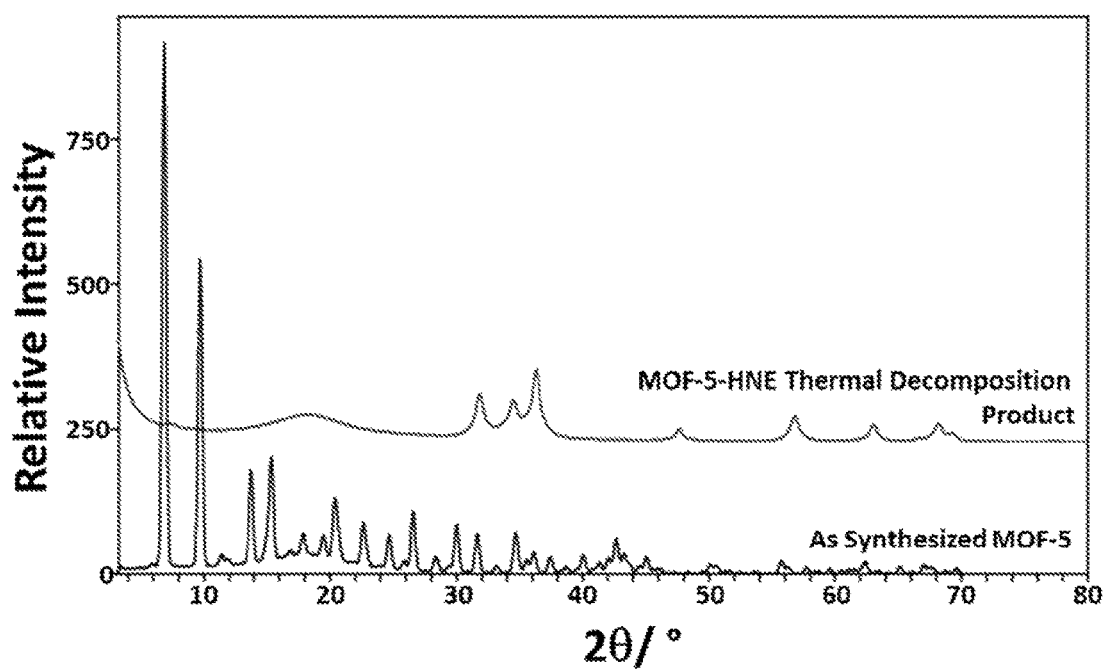

FIG. 13 is a graph showing PXRD of as synthesized MOF-5 (lower curve) and the thermal decomposition product of MOF-5-HNE (upper curve) showing the conversion of MOF-5-HNE to a mixture of carbon and zinc oxide.

Figure 14:
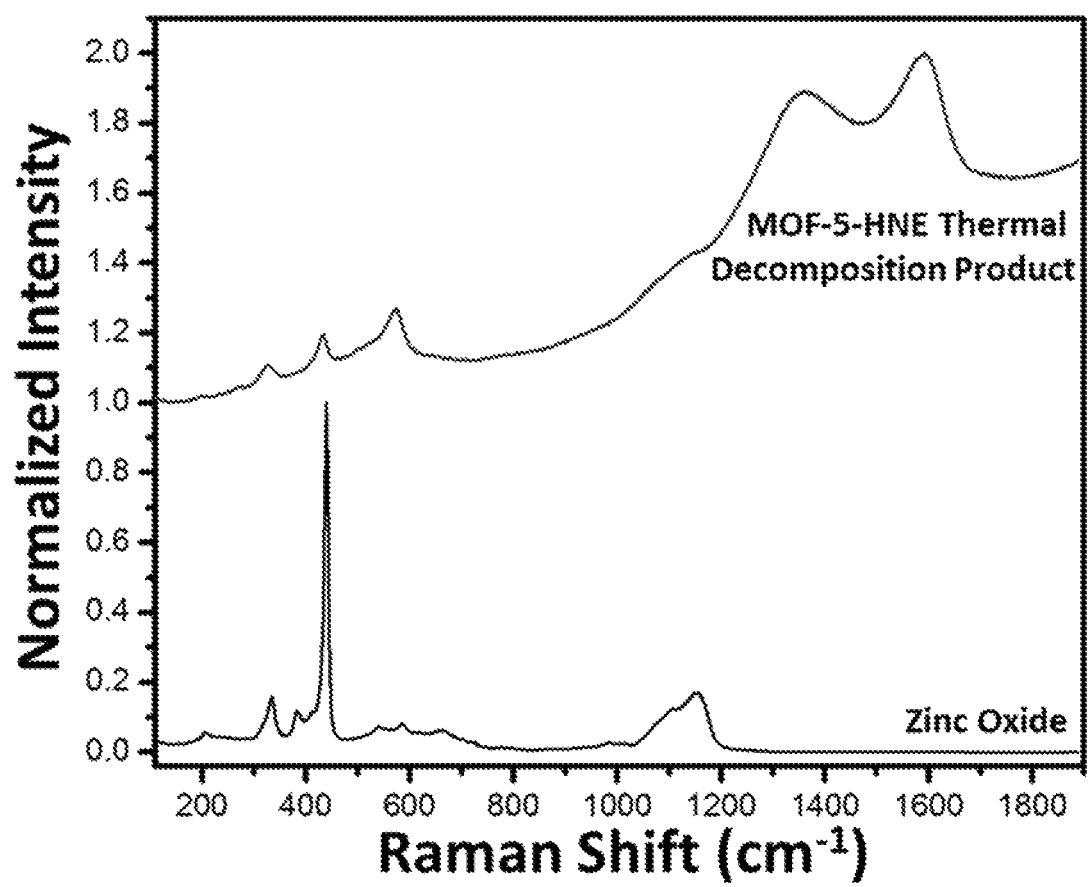

FIG. 14 is a graph showing Raman spectra of zinc oxide (lower curve) and the thermal decomposition product of MOF-5-HNE (upper curve) showing the conversion of MOF-5-HNE to a mixture of carbon and zinc oxide.

Figure 15:
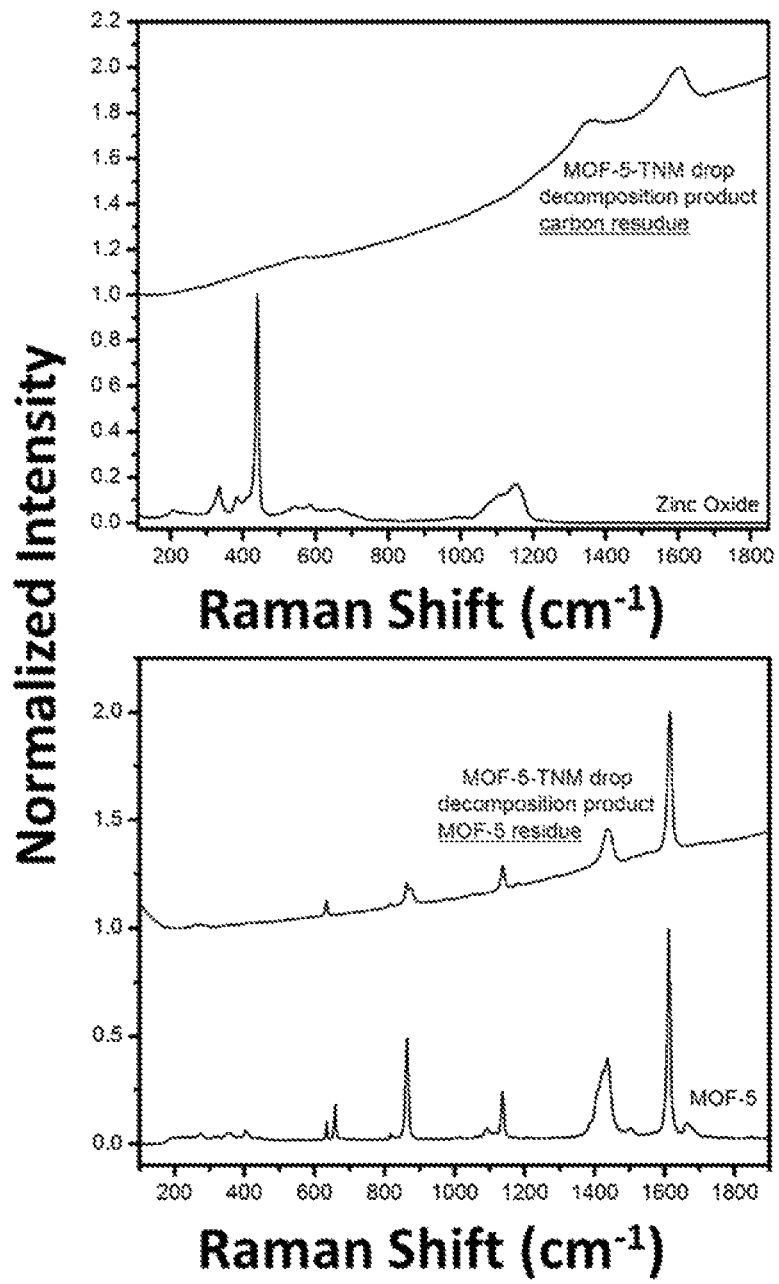

FIG. 15 are graphs showing Raman spectra of the impact decomposition products for MOF-5-TNM: (left) MOF-5-TNM decomposition product (carbon residue, upper) and zinc oxide (lower) for comparison and (right) MOF-5-TNM decomposition product (MOF-5 residue, upper) and MOF-5 for reference (lower).

Figure 16:
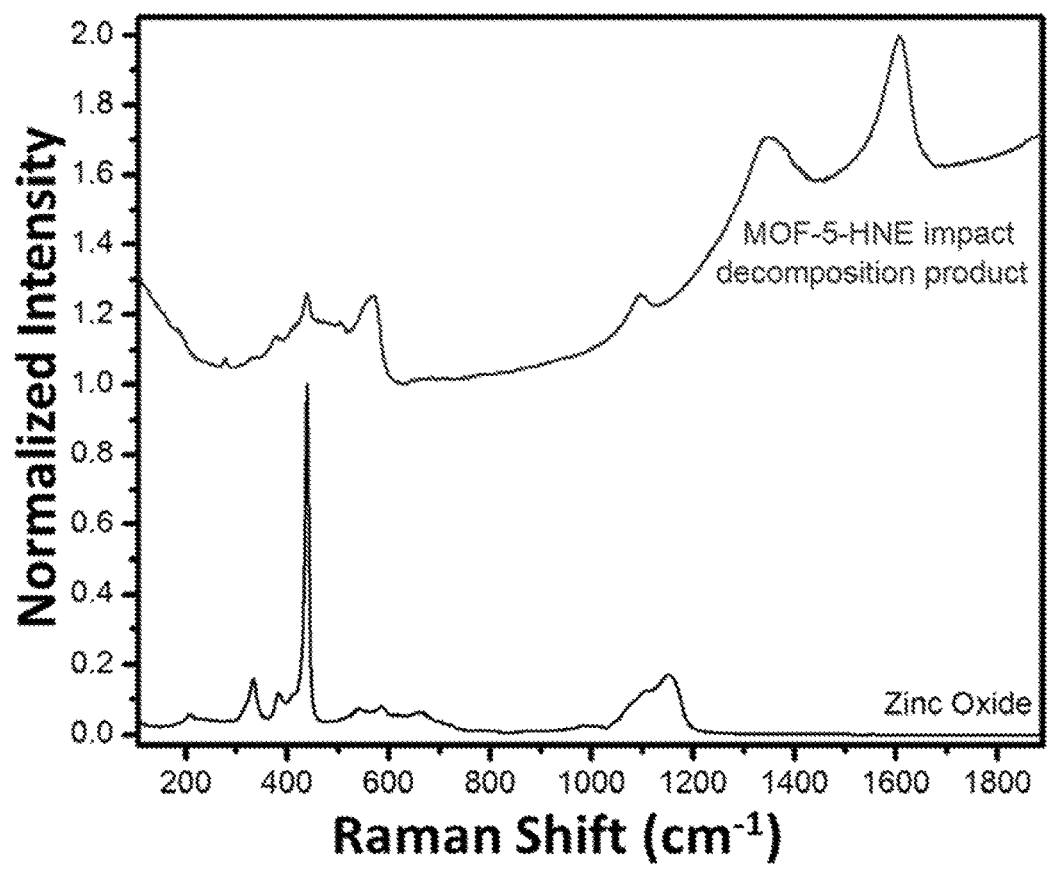

FIG. 16 is a graph showing Raman spectra of zinc oxide (lower curve) and the decomposition product of MOF-5-HNE (upper curve) after impact showing the conversion of MOF-5-HNE to a mixture of carbon and zinc oxide.

DETAILED DESCRIPTION

Description is provided of a composition or energetic composition where an energetic material, also called as an energetic molecule, an oxidant, or an oxidizer, is situated or held in the pores of a porous sorbent material, which in the broadest sense is named as a metal-organic framework. The process of getting the energetic material into the pores is described interchangeably as infiltrating, adsorbing, or entering, and the energetic material is said to be infiltrated, adsorbed, contained, disposed, situated, or held in the pores. In embodiments, the composition is called a host-guest complex in which the host is the sorbent and the guest is the energetic material or molecule.

In one embodiment, an energetic composition comprises a nanostructured sorbent and an energetic molecule, or oxidant, that is infiltrated into the pores of the sorbent. The sorbent is a crystalline porous coordination polymer, containing at least one metal node or cluster that is coordinated to an organic linker, forming a porous framework. In advantageous aspects, the second component, or oxidant, occupies the pore space of the sorbent, and is present in an amount such that the oxidant is at least 10% of the weight of the energetic composition. The combination of nanostructured sorbent (fuel) and oxidant forms a material more sensitive to detonation—such as by impact, friction, spark, or thermal stimulus—than one or both of the components.

In embodiments, the amount of oxidant in the pores of the sorbent is selected or adjusted to provide an oxygen balance (OB %) for the combination that is more favorable (i.e., closer to zero) than either of the individual components. For example, the combined components have OB % from −35% to +35% or from −10% to +10%. In various embodiments, the impact sensitivity of the energetic composition is greater than that of pentaerythritol tetranitrate (PETN), meaning the formulation acts as a primary explosive. The oxidant is either a liquid or a solid. If a liquid, the oxidant can be volatilized, for example by heating or by pulling a vacuum, so that the oxidant enters the pores of the sorbent through the vapor phase. If a solid, the solid material can be sublimed and infiltrated into the pores by the vapor phase. The oxidant is an organic nitro compound, an organic nitrate, or an oxygen rich organic compound, preferably one with a positive oxygen balance. Non-limiting examples include tetranitromethane (TNM) and hexanitroethane (HNE).

Surprisingly in light of the prior art, it has been found that infiltrating an energetic molecule into the pores of a sorbent such as an MOF yields an energetic composition that has a shock sensitivity that is actually greater than the shock sensitivity of the energetic molecule. (The energetic molecule is also referred to interchangeably herein as oxidant or oxidizer). Using the technology described herein, it is possible to take a secondary explosive and infiltrate it into the pores of an MOF to make an energetic composition that is a primary explosive. In effect, it is possible to turn a secondary explosive into a primary explosive by placing the energetic molecule in the pores of an MOF.

In various embodiments, the adsorption of oxidant into the nanostructured sorbent results in a material that displays greater heat released upon decomposition than would be expected for decomposition of an equivalent quantity of the pure components. In one aspect, the nanostructured sorbent is in the form of a metal-organic framework or microporous coordination polymer as further described herein. In various embodiments, the organic linker is selected from a carboxylate based organic molecule or a nitrogen-containing organic molecule.

In another embodiment, an energetic composition comprises a first component and second component. The first component is a nanostructured sorbent, exemplified by a metal organic framework, or MOF. The MOF is a crystalline porous coordination polymer and consists of at least one metal node or cluster that is coordinated to an organic linker forming at least one porous framework. The second component of the energetic composition is an oxidant molecule that is infiltrated into the pores of the sorbent such that the oxidant makes up 10% or greater of the mass of the energetic composition containing the sorbent and oxidant. Another way of saying this is that the energetic composition in these embodiments comprises preferably 10% by weight or more of the oxidant or energetic molecule.

As a result of combining the nanostructured sorbent as a fuel with the oxidant, an energetic composition is obtained that is more sensitive to detonation by impact, friction, spark, or thermal stimulus than either of the two components.

Advantageously in these embodiments and others, the weight ratio of oxidant to sorbent is such that the value of the oxygen balance of the composition is more favorable (i.e., closer to zero) than the value of the oxygen balance (OB%) of either of the components. In an embodiment, the oxygen balance of the resulting energetic composition is less than 35% and more than −35%. In other embodiments, the oxygen balance is less than 10% and more than −10%. In certain embodiments, the resulting energetic composition has an impact sensitivity greater than that of PETN and is considered to be a primary explosive. The oxidizer can be a liquid or a solid before it is infiltrated into the pores of the sorbent. Non-limiting examples include tetranitromethane and hexanitroethane.

In another embodiment, a host guest complex is provided that contains a sorbent molecule as described herein as the host and an energetic molecule as described herein as the guest. The guest is held in the pores of the host. The host is a metal-organic framework, or a MOF. The guest comprises an energetic molecule such as an organic nitrate ester or an organic nitro compound that is disposed within a pore of the host MOF. In preferred embodiments, the guest compound is characterized by an oxygen balance (OB %) of +30% or greater, where OB% is given by the formula $$OB\% = \frac{-1600}{\text{mol. wt. of compound}} \times \left(2X + \left(\frac{Y}{2}\right) + M - Z\right)$$

where X is the number of carbon atoms, Y is the number of hydrogen atoms, M is the number of metal atoms, and Z is the number of oxygen atoms.

In various embodiments, the OB% of the guest compound is greater than +35%, greater than +40%, greater than +45%, or greater than +50%. In various embodiments, the host guest complex is an energetic composition that is 20-80% by weight MOF and 80-20% of the guest compound. In preferred embodiments, the oxygen balance (OB%) of the energetic compound embodied in the guest-host complex is less than +35% and more than −35%;, less than +20% and more than −20%, or less than +10% and more than −10%.

The energetic composition of these teachings has two components, one of which provides pores for containing the other component within the pore. The resulting complex of the two components is referred to interchangeably herein as a host guest complex or as an energetic composition containing the two components. Thus, the host is the porous framework material most generically represented by the phrase metal-organic framework, or MOF. The MOF are also referred to as a microporous coordination polymer or MCP. Because of their porous nature, they serve as host components for the energetic molecules that are contained in their pores. In turn, the energetic material contained in the pores is interchangeably referred to as oxidizer, oxidant, guest, or energetic molecule. The first component is also referred to as a porous sorbent composition.

The nanostructured sorbent is made of a crystalline material known as microporous coordination polymer (MCP), or interchangeably as a metal-organic framework (MOF). In various embodiments, the porous material such as an MOF is made by reacting a source of a metal with an organic linker in a solvent in which both are soluble. In a non-limiting example, the organic linker and the metal source—a metal salt, carbonate or oxide, in non-limiting fashion—are partially or fully dissolved in an appropriate solvent and reacted. The reaction can occur in a closed vessel at elevated temperature or by subjecting the solution to microwaves, ultrasound, or electrochemical treatments. MOF materials can also be prepared by milling solid-phase metal derivatives and solid phase organic linkers in the presence of a liquid. As a result of the synthesis in the presence of the solvents, the resulting MOF material prepared from the reaction mixture normally includes at least some occluded solvent, which can be removed in a series of post-synthesis steps if desired. The product of synthesis, which is normally a crystalline MOF material, is isolated from the reaction mixture by precipitation, filtration, and other conventional means and optionally subjected to other steps to activate the material.

In the methods disclosed herein, the source of metal for the initial reaction to form the MOF is selected from suitable soluble sources, including salts such as nitrates, carbonates, oxides, acetates, and the like. The identity of the metal is not necessarily limited. In various embodiments, the source of metal includes a metal cation selected from $Zn^{2+}$, $Cu^{2+}$, $Mg^{2+}$, $Ni^{2+}$, $Co^{2+}$, and $Ni^{2+}$. Zinc nitrate and copper (II) nitrate are common starting materials. Commercially available hydrates can be used.

The source of metal is reacted with an organic linker composition in a solvent system to form a MOF. The organic linker composition contains one or more organic compounds that serve as linkers in the MOF. In one embodiment, the linker compositions contain one or more organic compounds that contain two or more carboxyl groups. In various embodiments, the linker contains two or more carboxyl groups that are attached to an aromatic ring of the linker. In other embodiments, the linker contains two or more nitrogen containing aromatic rings. In other embodiments, the linker is a compound that contains two or more imidazole rings, or two or more nitrogen heterocycles such as imidazole, tetrazole, and pyridine, or two or more nitrogen containing heterocycles. The following table provides additional examples of suitable linkers, which are commercially available.

TABLE

| Structure | Chemical Name |
|---|---|
| [9,10-anthracenedicarboxylic acid structure] | 9,10-Anthracenedicarboxylic acid |
| [biphenyl-3,3',5,5'-tetracarboxylic acid structure] | Biphenyl-3,3',5,5'-tetracarboxylic acid |
| [biphenyl-3,4',5-tricarboxylic acid structure] | Biphenyl-3,4',5-tricarboxylic acid |

TABLE-continued

| Structure | Chemical Name |
| --- | --- |
| 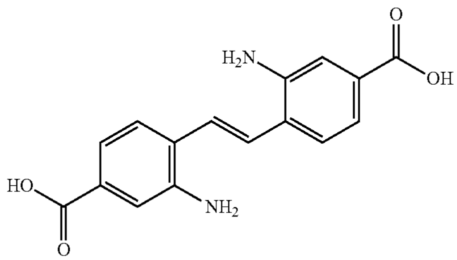 | 2,2'-Diamino-4,4'-stilbenedicarboxylic acid |
| 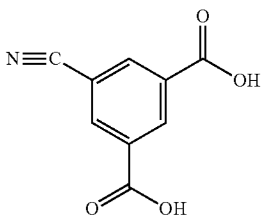 [SMILES: N#Cc1cc(C(=O)O)cc(C(=O)O)c1] | 5-Cyano-1,3-benzenedicarboxylic acid |
| 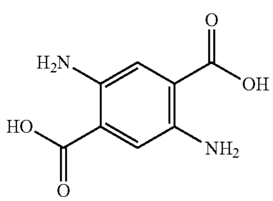 [SMILES: Nc1cc(C(=O)O)c(N)cc1C(=O)O] | 2,5-Diaminoterephthalic acid |
| 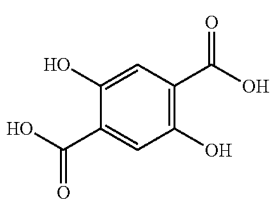 [SMILES: O=C(O)c1cc(O)c(C(=O)O)cc1O] | 2,5-Dihydroxyterephthalic acid |
| 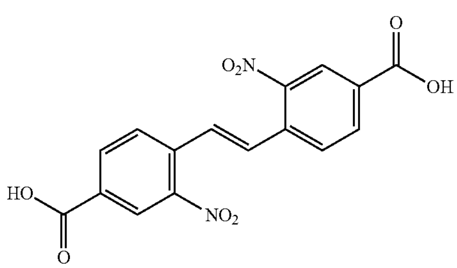 [SMILES: O=C(O)c1ccc(/C=C/c2ccc(C(=O)O)cc2[N+](=O)[O-])c([N+](=O)[O-])c1] | 2,2'-Dinitro-4,4'-stilbenedicarboxylic acid |
| 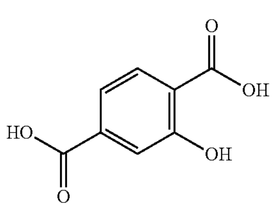 [SMILES: O=C(O)c1ccc(C(=O)O)c(O)c1] | 2-Hydroxyterephthalic acid |
| 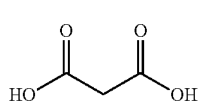 | malonic acid |

TABLE-continued

| Structure | Chemical Name |
|---|---|
| 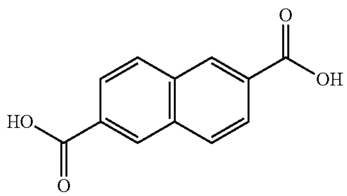 [SMILES: O=C(O)c1ccc2cc(C(=O)O)ccc2c1] | 2,6-Naphthalenedicarboxylic acid |
| 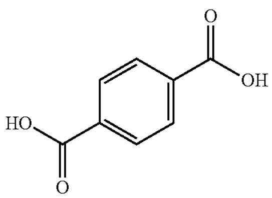 [SMILES: O=C(O)c1ccc(C(=O)O)cc1] | terephthalic acid |
| 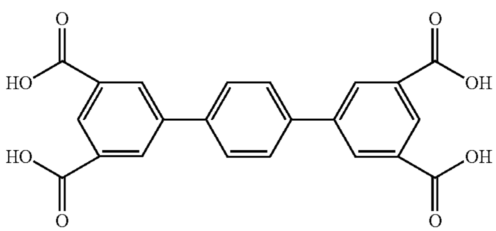 [SMILES: O=C(O)c1cc(C(=O)O)cc(-c2ccc(-c3cc(C(=O)O)cc(C(=O)O)c3)cc2)c1] | [1,1':4',1'']Terphenyl-3,3'',5,5''-tetracarboxylic acid |
| 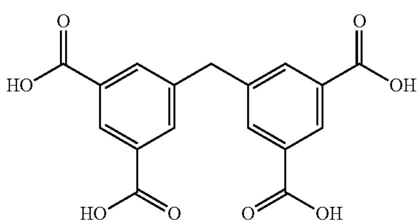 [SMILES: O=C(O)c1cc(Cc2cc(C(=O)O)cc(C(=O)O)c2)cc(C(=O)O)c1] | 3,3',5,5'-Tetracarboxydiphenylmethane |
| 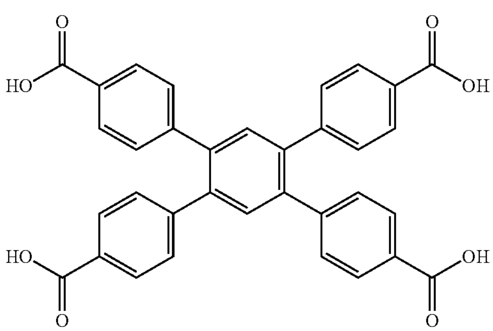 [SMILES: O=C(O)c1ccc(-c2cc(-c3ccc(C(=O)O)cc3)c(-c3ccc(C(=O)O)cc3)cc2-c2ccc(C(=O)O)cc2)cc1] | 1,2,4,5-Tetrakis(4-carboxyphenyl)benzene |
| 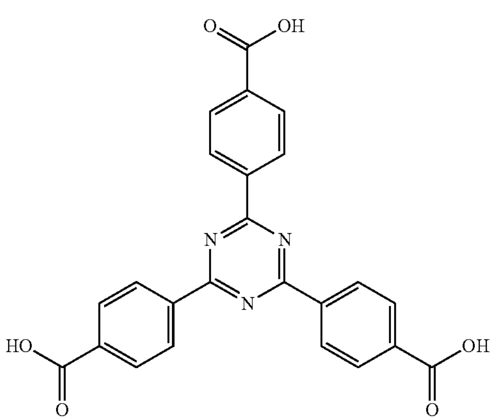 [SMILES: O=C(O)c1ccc(-c2nc(-c3ccc(C(=O)O)cc3)nc(-c3ccc(C(=O)O)cc3)n2)cc1] | 4,4',4''-s-Triazine-2,4,6-triyl-tribenzoic acid |

TABLE-continued

| Structure | Chemical Name |
| --- | --- |
| 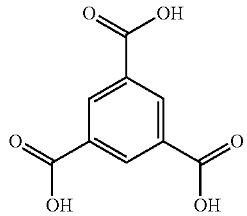 [SMILES: O=C(O)c1cc(C(=O)O)cc(C(=O)O)c1] | trimesic acid, or benzene-1,3,5-tricarboxylic aicd |
| 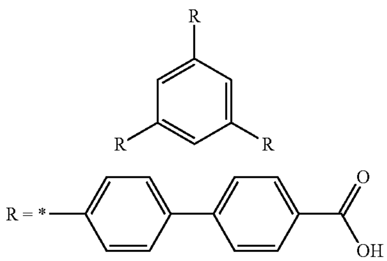 | 1,3,5-Tris(4'-carboxy[1,1'-biphenyl]-4-yl)benzene |
| 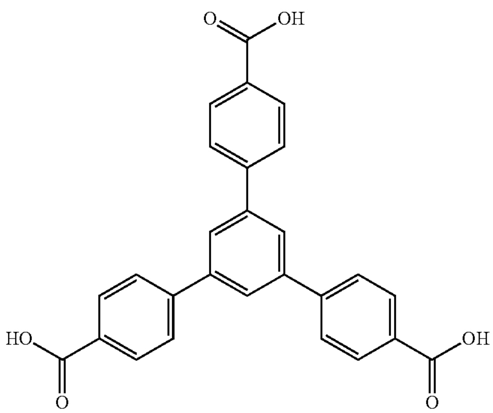 [SMILES: O=C(O)c1ccc(-c2cc(-c3ccc(C(=O)O)cc3)cc(-c3ccc(C(=O)O)cc3)c2)cc1] | 1,3,5-Tris(4-carboxyphenyl)benzene |
| 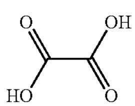 | ethanedioic acid |
| 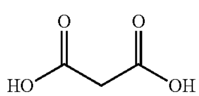 | propanedioic acid = malonic acid |
| 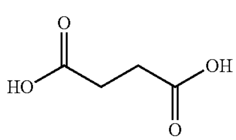 | butanedioic acid |
| 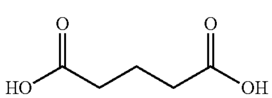 | pentanedioic acid |
| 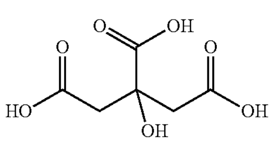 [SMILES: O=C(O)CC(O)(CC(=O)O)C(=O)O] | citric acid |

TABLE-continued

| Structure | Chemical Name |
|---|---|
| 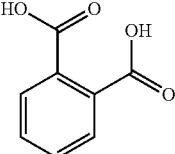 | phthalic acid |
| 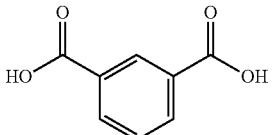 | isophthalic acid |

*BTE = 4,4',4''-[benzene-1,3,5-triyl-tris(ethyne-2,1-diyl)]tribenzoate
*BDPC = biphenyl-4,4'-dicarboxylate
BDC = 1,4-benzenedicarboylate = terephthalic acid above
BTT = benzene-1,3,5-tris(1H-tetrazole)
imidazole
2-methylimidazole There are a wide variety of MCP materials known in the literature. They are also characterized as metal-organic frameworks, or MOFs. As noted, the terms MCP and MOF are used interchangeably to denote the component of the guest host complex that provides the porous structure of the sorbent. One series is denoted in the literature as MOF-x, where x is an integer. For example, MOF-1 through MOF-215 are known. In another series, the MOF materials are designated as IRMOF-y, where y similarly is an integer assigned to differentiate. In general, the MOF-x and the IRMOF-y materials are synthesized from starting metal sources and organic linkers as described herein.

Generally, for a solid to be labeled as a Metal-Organic Framework (MOF), it should display the inherent attributes the term implies. These include strong bonding and a geometrically well-defined structure. The MOF materials tend to be characterized by relatively high levels of surface area, making them useful for a variety of applications such as catalysis and gas storage.

Microporous coordination polymers (MCPs) and methods of making MCPs are well known in the art. Generally, MCPs are polymers and most typically three-dimensional coordination complexes that include a plurality of inorganic metal clusters linked together by a plurality of linking ligand compounds. The inorganic metal clusters can include a plurality metals connected by a plurality of bridging moieties. The metals of the clusters can be cationic and are generally hexacoordinate, pentacoordinate, tetracoordinate, or a mixture thereof. In one embodiment, each metal cluster is the same. In an alternative embodiment, the make-up of the metal cluster can differ throughout the MCP. For example, a MCP may be comprised of 2 or 3 different metal clusters. The inorganic metals and linking ligands may be chosen such that the overall MCP framework has a net charge. A description of suitable MCPs for use as the nanostructured sorbent of the disclosure can be found in U.S. Pat. No. 9,353,129 (U of M 5043); U.S. Pat. No. 8,425,659 (U of M 3932); U.S. Pat. Nos. 7,202,385; 7,196,210; 6,930,193; 6,929,679; and 5,648,508 and in U.S. Patent Application Publication Nos. 2014/0179514 (U of M 5589); 2013/0305922 (U of M 5191); 2007/0068389; 2006/0252641; 2006/0185388; 2006/0154807; 2005/0192175; and 2005/0154222; the respective disclosures of which are hereby incorporated by reference in their entireties.

A particular kind of metal organic framework, or MOF, is called a zeolitic imidazolate framework, or ZIF. ZIF are described for example in proceedings of the National Academy of Sciences, 2006, Vol. 103, pp. 10186-10191, the disclosure of which is incorporated herein by reference. The ZIF are a class of metal organic frameworks that are topologically isomorphic with zeolites. They are composed of tetrahedrally coordinated transition metal ions (e.g., Fe, Co, Cu, Zn) connected by linkers that are imidazolates. Since the metal-imidazole-metal angle is similar to the 145° Si—O—Si angle in zeolites, the ZIFs tend to have zeolite-like topologies. As used herein, the ZIFs should be considered to be a subset of the MOF.

In various embodiments, the MOFs are activated after synthesis under conditions of flowing supercritical carbon dioxide as described in US patent publication US2014/0179514 (U of M 5589), the disclosure of which is incorporated by reference.

Energetic Materials

In various embodiments, the following are examples of organic energetic materials that can be infiltrated into the pores of a microporous coordination polymer using the solid phase or vapor phase methods described herein : 2,4,6,8,10,12-hexanitro-2,4,6,8,10,12-hexaazaisowurtzitane (CL-20); 5-nitro triazol-3-one (NTO); 2,4,6-trinitrotoluene (TNT); 1,3,5,7-tetranitro-1,3,5,7-tetrazocane (HMX); trinitro triamino benzene (TATB); 3,5-dinitro-2,6-bis-picrylamino pyridine (PYX); nitroglycerine (NG); ethylene glycol dinitrate (EGDN); ethylenedinitramine (EDNA); diethylene glycol dinitrate (DEGDN); Semtex; Pentolite; trimethylol ethyl trinitrate (TMETN); tetryl, hexahydro-1,3,5-trinitro-1,3,5-triazine (RDX); pentaerythritol tetranitrate (PETN); 2,2,2-trinitroethyl-4,4,4-trinitrobutyrate (TNETB); methylamine nitrate; nitrocellulose; $N^3, N^3, N^{t3}, N^{t3}, N^7, N^7, N^{t7}, N^{t7}$-octafluoro-1,5-dinitro-1,5-diazocane-3,3,7,7-tetraamine (HNFX); nitroguanidine; hexanitrostilbene; 2,2-dinitroethene-1,1-diamine (FOX-7); dinitrourea; and picric acid. In various aspects, the energetic material is selected from the group consisting of 2,4,6-trinitrotoluene (TNT), and 1,3,5,7-tetranitro-1,3,5,7-tetrazocane (HMX). Further examples include tetranitromethane (TNM) and hexanitroethane (HNE).

In one embodiment, the energetic material is a primary explosive, meaning it has a sensitivity higher than PETN. The current teachings thus show how to increase the sensitivity of primary explosives to make them more effective. In another embodiment, the energetic material is a secondary explosive, meaning it has a sensitivity lower than that of PETN. In such embodiments, the current teachings provide a way of taking a secondary explosive and turning it into a primary explosive by infiltrating the energetic material into the pores of the sorbent MOF.

Guest Host Complexes

Energetic guest host complexes contain relatively high loadings of energetic material in the pores of a nanostructured sorbent such as an MOF. They are prepared using liquid or vapor techniques in which energetic molecules are infiltrated into the porous framework of the sorbent. The amount of infiltrated energetic material can be measured and expressed as a weight percent using thermogravimetric techniques described herein.

In various embodiments, the guest-host complexes are characterized by a weight % content of at least 10% and up to 85% or 90% of the energetic molecule. Because of this high loading, the highly negative oxygen balance of the MOF materials can be balanced by infiltrating an energetic material having a positive oxygen balance, to achieve a guest host structure having an oxygen balance close to zero. In various embodiments, the oxygen balance is from −35% to +35%, from −30% to +30%, from −20% to +20%, from −15% to +15%, from −10% to +10%, and from −5% to +5%. If desired, the guest host complex can be synthesized to a desired oxygen balance by exposing the sorbent component to a vapor of energetic compound for a time sufficient to infiltrate an amount of energetic material that gives the theoretical desired oxygen balance. Two examples of energetic materials with high positive oxygen balance are tetranitromethane (TNM) and hexanitroethane (HNE).

Synthesis of complexes

Complexes can be made using liquid methods as disclosed in U.S. Pat. No. 8,506,734, the disclosure of which is hereby incorporated by reference. Especially by using energetic materials with highly positive oxygen balance, complexes with an overall low oxygen balance can be made. This is because the host molecules (MOFs) have highly negative OB%.

In certain embodiments, molecules of the energetic materials are infiltrated into the pores of the sorbent using vapor methods. Liquid energetic materials are infiltrated by vapor diffusion into the pores, while solid materials are subjected to sublimation conditions (such as pulling a vacuum) and the vapor phase molecules diffuse into the pores. Advantageously, in the vapor phase methods there is minimal competition in the pores from solvent molecules or other impurities. It has been observed that especially the sublimation methods incorporate high levels of energetic materials into the pores of the sorbent. Advantageously, the guest-host complexes made in this way contain essentially no solvent molecules in the pores.

Explosive Properties

The energetic compositions disclosed herein contain a nanostructured sorbent that serves as a fuel, and further comprises an energetic material disposed in the pores of the sorbent. Examples of sorbent include the known class of microporous coordination polymer (MCP) or metal organic framework (MOF) used interchangeably. The energetic material serves as an oxidant or oxidizer. The sorbent and the oxidizer are thus two components of the energetic compositions. The latter is characterized in many cases as having an impact sensitivity higher than the sorbent or the oxidizer alone. In other aspects, the guest-host complex embodying the energetic composition displays greater heat released upon decomposition than would be expected for decomposition of an equivalent quantity of the individual components.

EXAMPLES

MCPs can serve as host frameworks for the incorporation of oxidant guest molecules leading to the molecular scale mixing of fuel and oxidizer in an energetic intimate mixture. The adsorption of oxidants tetranitromethane (TNM) and 1,1,1,2,2,2-hexanitroethane (HNE) into MOF-5 (Metal-Organic Framework-5, [$Zn_4O(BDC)_3$]$_n$; BDC=1,4-benzenedicarboxylate) is demonstrated here to be successful for the development of energetic materials based on the intimate mixing of fuel and oxidant species. Furthermore, when considering the oxygen balance of MOF-5 (−93.6%), the inclusion of oxidizing guest molecules with positive oxygen balances, such as TNM (OB=+49.0%) and HNE (OB=+42.7%), will lead to an energetic material with an overall more neutral oxygen balance compared to existing explosives.

By contrast, vapor diffusion, in the case of MOF-5-TNM, and sublimation, in the case of MOF-5-HNE, were investigated and were found to effectively control composition of the composite. MOF-5-TNM was prepared by placing a 4 mL vial containing MOF-5 (10.0 mg) into a 20 mL vial containing TNM (0.20 mL). The vial was allowed to sit, sealed, at room temperature. MOF-5-HNE was synthesized by placing HNE (25.0 mg) into a Schlenk flask, which also contained a small boat of MOF-5 (10.0 mg). The Schlenk flask was placed under vacuum and the HNE was allowed to sublime and adsorb into the pores of MOF-5. Powder X-ray diffraction (PXRD) shows that the structural integrity of the MCP was retained upon loading of the TNM and HNE oxidants (FIG. 3 and FIG. 4).

Figure 1:
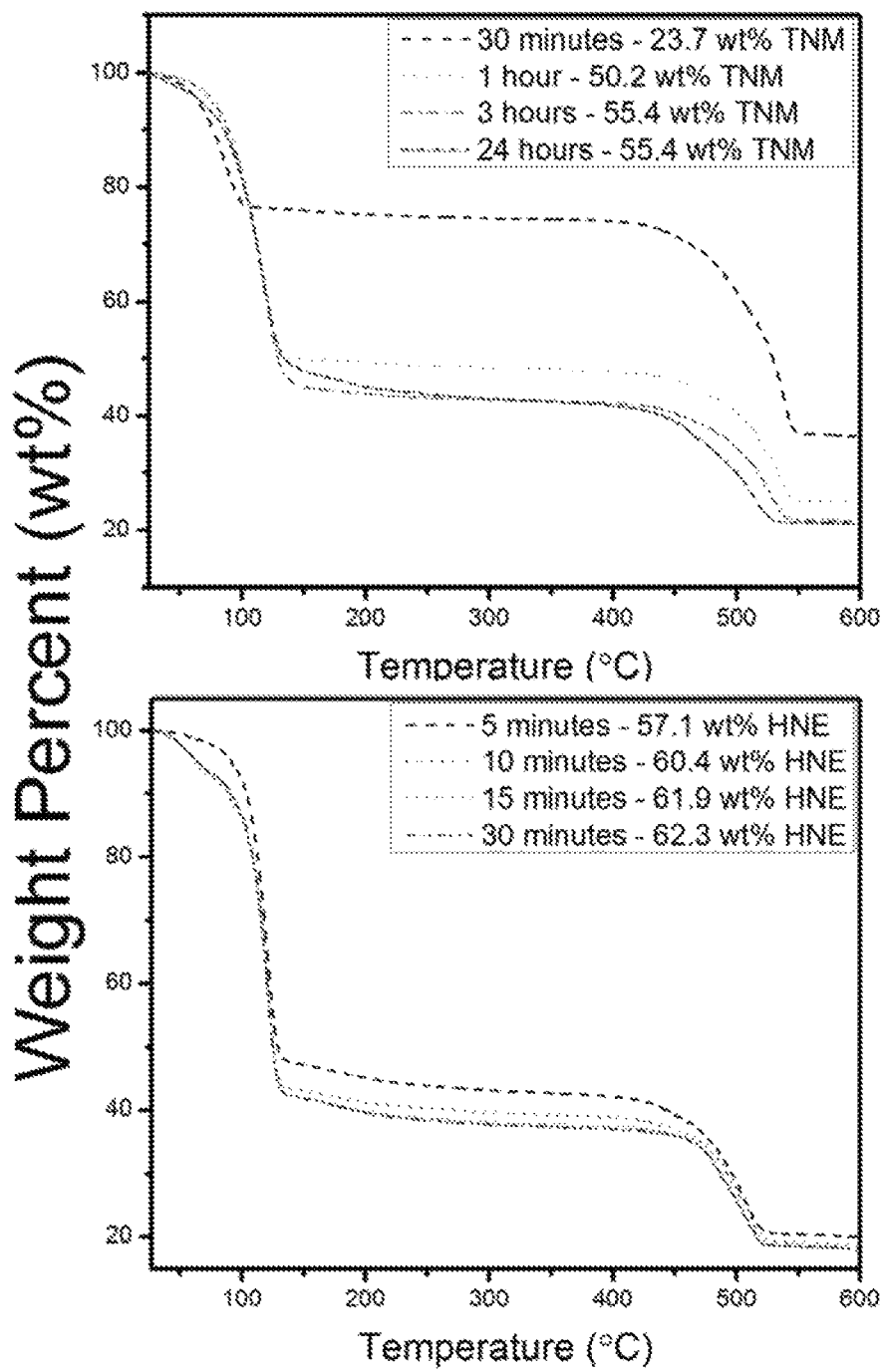
FIG. 1 shows Thermogravimetric Analysis (TGA) of the adsorption of TNM (a) and HNE (b) into MOF-5 carried out for different periods of time.

Thermogravimetric analysis (TGA) was used to quantify the amount of TNM and HNE adsorbed into the MCP and to monitor the amount of oxidant adsorbed as a function of loading time. In addition, the data obtained from TGA experiments was used to calculate the oxygen balance of the loaded MOF-5. As expected, the weight percent of each oxidant loaded into MOF-5 increases with time until the pores are saturated. For MOF-5-TNM, it was determined that the MCP could adsorb as much as about 55 wt % TNM as quickly as in 3 hours (FIG. 1a). This translates to an oxygen balance of −14.6 % and can be compared to the oxygen balance of the guest free MOF-5 of −94%. For MOF-5-HNE, the adsorption of HNE into MOF-5 saturated at about 62 wt %; this translates to an oxygen balance of −8.70% (FIG. 1b). The oxygen balance of the composite materials is neutral compared to many existing and commonly used explosive materials (TNT=−73.9%, RDX/HMX=−21.6%). In addition, the oxygen balances are among the best reported for energetic coordination polymer-based materials.

In order to quantify the retention of the oxidant guests in the MCP host, vapor pressure of the oxidants was evaluated before and after loading into the MCP. These experiments were carried out by loading the MCP, saturated with oxidant, into crimped aluminum DSC pans with 50 μm holes in their lids. The mass loss of the samples was monitored at 30° C. for MOF-5-TNM and 45° C. for MOF-5-HNE under a 30 mL/min flow of nitrogen gas for 10 hours. Compared to the pure oxidants, the composites exhibit a reduced rate of mass loss, indicating that the volatility of the oxidant is suppressed upon adsorption into the MCP. The volatility was suppressed by ~75× for MOF-5-TNM system and ~3× for MOF-5-HNE system (FIG. 9 and FIG. 10). The suppression of oxidant volatility can be advantageous for improved handling and stability of the energetics.

Figure 2:
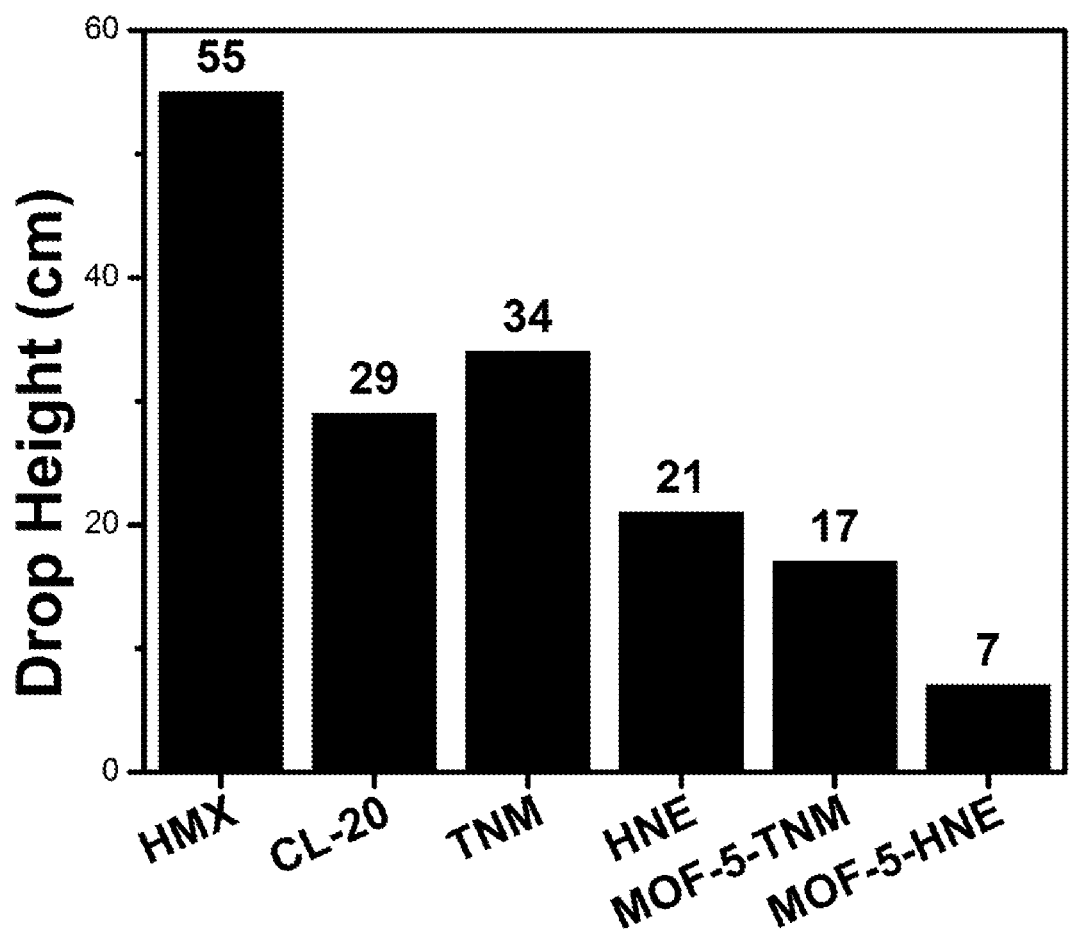
FIG. 2 is a bar graph comparing the sensitivity measurements for the determination of the $D_{50}h$, or 50% probability of detonation, for HMX, CL-20, TNM, HNE, MOF-5-TNM, and MOF-5-HNE.

Sensitivity measurements were conducted to quantify the effects of oxidant adsorption on the impact sensitivity of the resulting MCP-oxidant materials. The measurements were performed using a small-scale drop height apparatus, which utilizes non-hermetic DSC pans to encase a small amount of sample (2.00 mg ±10%) onto which a 5 lb weight was dropped from a pre-measured height. The oxidant molecules TNM and HNE exhibit a $D_{50}h$, or 50% probability of detonation, when dropped from heights of 34 and 21 cm, respectively, on this apparatus while MOF-5, as expected, shows no energetic behavior up to the maximum drop height of the apparatus. Adsorption of these oxidants into MOF-5 results in energetics with $D_{50}h$ values of 17 cm and 7 cm for MOF-5-TNM and MOF-5-HNE, respectively (FIG. 2). This would classify these materials as primary explosives, or energetics that are extremely sensitive to external stimuli (like for example pentaerythritol tetranitrate), and can be contrasted with insensitive energetics, known as secondary explosives (such as octahydro-1,3,5,7-tetranitro-1,3,5,7-tetrazocine or HMX, FIG. 2). Here, HNE, a secondary explosive, is rendered primary by adsorption into MOF-5. TNM, lying close to the cutoff between primary and secondary explosives, is rendered more sensitive upon adsorption into MOF-5. The increase in sensitivity is worthwhile considering the facile synthesis by which these primaries can be produced, particularly bearing in mind the safer transportation of the individual components during shipment.

In order to evaluate the performance of the saturated MCP-oxidant energetic materials (also referred to as the energetic compositions or host-guest complexes), differential scanning calorimetry (DSC) was employed. Initial experiments were performed using standard hermetically sealed aluminum pans and it was observed that the heat evolution increased as a function of increasing heating rate for both MOF-5-TNM and MOF-5-HNE. It was hypothesized that this heating rate dependence was due to desaturation of oxidant from the MCP framework as a function of temperature. Furthermore, the pressure generated by thermal decomposition of both the oxidants and loaded MCPs exceeded the pressure limit in the standard hermetically sealed pans and, therefore, gas escape from the DSC pans resulted, even using sub-milligram quantities of sample. This problem was overcome with stainless steel, high-pressure, DSC pans. The thermal lag, however, at higher ramp rates prevented the use of the high-pressure pans at ramp rates sufficiently fast to avoid oxidant desaturation. In order to show that incorporation of the oxidants into MOF-5 results in an increased heat release, excess oxidant was added to the DSC pans along with the loaded MCPs resulting in equilibration of oxidant vapor pressure in the pan therefore preventing desaturation of the oxidants from the pores. We theorize that if MOF-5 is not providing any additional heat, then the heat released for the loaded MOF-5 with excess oxidant would not increase, but rather be potentially decreased relative to the neat oxidant due to the additional mass of MOF-5 in the pan. The exothermic events in DSC thermograms were integrated to give the heat released upon decomposition (FIG. 6, FIG. 7 and FIG. 8). Thermal decomposition of neat TNM results in the generation of 1146 J $g^{-1}$. The thermal decomposition of MOF-5-TNM by DSC results in a heat release of 690 J $g^{-1}$. This observation is consistent with TNM escaping from the framework, under these conditions, and decomposing outside of MOF-5. When a small excess of TNM is added to a MOF-5-TNM crystal inside the high pressure DSC pan, the heat is markedly increased from 1146 J $g^{-1}$, for neat TNM, to 5749 J $g^{-1}$, for MOF-5-TNM with excess TNM. We attribute the increased heat released, to the oxidant which is able to react with MOF-5 since escape from the framework is not as favorable under an excess TNM atmosphere. Moreover, the clear shift of the peak temperature in the DSC thermograms from 202° C., for neat TNM, to 197° C., for MOF-5-TNM, and associated dramatic peak sharpening is indicative of an increase in the thermal sensitivity of the material. For HNE, thermal decomposition results in a heat release of 2138 J $g^{-1}$, whereas MOF-5-HNE shows a heat release of 2476 J $g^{-1}$. This slight increase in the heat released is indicative of an exothermic reaction between MOF-5 and HNE. When excess HNE was added to a high pressure DSC pan containing MOF-5, the heat released was increased to 4455 J $g^{-1}$. We theorize that partial escape of HNE from the framework is suppressed when excess HNE is added, the heat released is even more increased due to retention of HNE in the framework and therefore increased reactivity between MOF-5 and HNE. Analogous to the MOF-5-TNM case, the decomposition temperature of MOF-5-HNE is shifted to a lower temperature relative to HNE. MOF-5-HNE has a peak temperature at 135° C. which is notably lower than neat HNE at 153° C., indicating an increased thermal sensitivity of the oxidant upon incorporation into the MOF-5 lattice. These data indicate that incorporation of the oxidants into MOF-5 leads to increased heat released upon thermal decomposition of loaded MOF-5 relative to the neat oxidants and is consistent with a the framework acting as a fuel for the oxidizing energetic guest.

In light of the observed heating rate dependence, analysis of the decomposition products was performed on residue collected after thermal initiation (FIG. 11, FIG. 12, FIG. 13 and FIG. 14). We hypothesize that the volatility of TNM adsorbed into MOF-5 is not sufficiently suppressed to result in an efficient reaction between fuel and oxidant, particularly upon thermal initiation. Raman spectroscopy and PXRD of the crystals collected after thermal initiation confirms that the MOF-5 crystal structure is still intact.

Analogous to the previously discussed decomposition product analysis, drop test pans were opened and analysis of the residue coating the inside of the pan was performed to highlight the differences between these materials behavior to initiation by impact and thermal initiation methods.

For MOF-5-TNM the decomposition product by impact was determined by Raman spectroscopy to be a mixture of carbon and un-reacted MOF-5 (FIG. 15). These data demonstrate that MOF-5-TNM does not undergo efficient reaction by impact or thermal initiation under the conditions explored. HNE, having a much lower volatility than TNM is likely to remain intimately mixed for efficient reaction with MOF-5. This is evident by noting that the heat released for MOF-5-HNE alone is notably higher than pure HNE; this differs from the TNM/MOF-5-TNM system. We hypothesize that MOF-5-HNE results in a more efficient reaction between fuel and oxidant upon both impact and thermal initiation. MOF-5-HNE is completely decomposed upon thermal initiation into a mixture of carbon and zinc oxide; this was confirmed by Raman spectroscopy and PXRD (FIGS. 13 and 14). The same was shown to be true for MOF-5-HNE initiated by impact (FIG. 16).

To conclude, employing non-energetic MCPs as hosts (fuel) for the adsorption of oxidant molecules enables the intimate and molecular scale mixing of fuel and oxidizer on a level that is not commonly achievable in traditional energetic mixtures. The adsorption of the oxidants into MOF-5 resulted in increased heat released upon decomposition, which shows potential for utilization of this method as a platform to develop high-performance energetic materials. This simple strategy can therefore be applied to other MCPs and oxidants for the further development of energetic materials with high density, desirable oxygen balance, and increased heats of detonation. Furthermore, adding additional adsorptive sites to the framework can optimize interactions between the host and guest; which can potentially further reduce the volatility of guest molecules and influence properties such as sensitivity.

1. Experimental Procedures

Caution: Although no unplanned detonations were encountered during this work, TNM, HNE, MOF-5-TNM and MOF-5-HNE are all dangerous explosives. Proper safety practices and equipment was used to prevent an explosion due to friction, heat, static shock, or impact. Be aware that the potential for severe injury exists if these materials are handled improperly.

Synthesis of MOF-5. MOF-5 was synthesized by a method previously reported in the literature.

Activation. Samples were activated by exposure to a dynamic vacuum ($10^{-2}$ Torr) for 24 hours.

Synthesis of Hexanitroethane (HNE). HNE was synthesized by a method previously reported in the literature.

MOF-5-TNM. For the adsorption of TNM, 10.0 mg of MOF-5 was weighed into a 4 mL vial in an $N_2$ filled glovebox. Outside of the glovebox, TNM (0.20 mL) was added to a 20 mL scintillation vial, capped, and allowed to come to equilibrium with the atmosphere in the vial. The 4 mL vial containing the MOF-5 was removed from the glovebox, opened to air, inserted into the 20 mL vial containing TNM, and capped. TNM was allowed to vaporize, come to equilibrium with the chamber, and adsorb into MOF-5 for variable amounts of time. To stop the adsorption, the 4 mL vial (containing MOF-5-TNM) was removed from the chamber and capped.

MOF-5-HNE. For the adsorption of HNE, 10.0 mg of MOF-5 was weighed into a 4 mL vial in a $N_2$ filled glovebox. The sample was then removed from the glovebox and transferred to a small aluminium boat. This boat was inserted into a schlenk tube containing 25.0 mg of HNE. The schlenk tube was connected to a vacuum line and carefully evacuated to 50 mTorr, then closed. HNE was allowed to sublime in the chamber and adsorb into MOF-5 for variable amounts of time. The adsorption was stopped by releasing the vacuum in the chamber, the product (MOF-5-HNE) was collected in a 4 mL vial, and capped.

Powder X-ray diffraction. Powder X-ray diffraction (PXRD) patterns were collected using a Rigaku R-axis Spider diffractometer with an image plate detector and graphite monochromated Cu-Kα radiation (1.5406 A). The patterns were collected with the tube operating at 40 kV and 44 mA. Images were collected in transmission mode with x set at 45°, φ rotating at 10° /min, and ω oscillating between 5° and 50° to minimize the effects of preferred orientation. Integration of the resulting images was performed in the AreaMax (2.0) software package with a step size of 0.1 in 2θ.

Gas sorption measurements. Sorption experiments were carried out using a NOVA e-series 4200 surface area analyser (Quantachrome Instruments, Boynton Beach, Florida, USA). $N_2$ (99.999%) was purchased from Cryogenic Gases and used as received. For $N_2$ measurements, a glass sample cell was charged with ~20 mg sample and analysed at 77 K. Sorption isotherms were collected in the NOVAwin software.

Thermogravimetric Analysis. A TA Instruments Q50 TGA was used to obtain thermogravimetric data in which the analyte was heated from ~25° C. to 600° C. at a rate of 10° C/min and analysed in a platinum pan under flowing nitrogen.

Vapor pressure measurements. Vapour pressure experiments (shown in Figure S4 and S5) were performed as previously described.[3] In this case, the degree by which the vapour pressure was suppressed was calculated by dividing the slope of the weight loss of the pure oxidant by the slope of weight loss of the MCP-oxidant mixture.

Differential Scanning calorimetry. Thermograms of each sample were recorded on a TA Instruments Q10 DSC. All experiments were run using a Tzero™ DSC High Pressure Capsule Kit and studied under a nitrogen purge with a heating rate of 20° C/min, covering the temperature range of ~100 ° C. to ~300° C. Calibration of the instrument was performed using an indium standard. Thermograms were analysed using TA Universal Analysis 2000, V 4.5A.

Raman Spectroscopy. Raman spectra were obtained using a Renishaw inVia Raman microscope equipped with a CCD detector, 785 nm laser, 1200 lines/mm grating, and 65 pm slit was used for collecting data. Spectra were collected using a static scan mode and analysed using the Wire 4.2 software package. Calibration of the instrument was performed using a silicon standard for all experiments.

2. Oxygen Balance Determination

The oxygen balance calculation for individual components such as the guest and host molecules is performed using the standard method using the equation shown below.

$$OB\% = \frac{-1600}{\text{mol. wt. of compound}} \times \left(2X + \left(\frac{Y}{2}\right) + M - Z\right)$$

where X is the number of carbon atoms, Y is the number of hydrogen atoms, M is the number of metal atoms, and Z is the number of oxygen atoms.

For the loaded samples, the oxygen balance was determined as shown in the following illustrative example (using data collected from TGA):

First, the TNM weight percent in the total composite is extracted from the TGA experiment. To give an example, TNM weight percent is 55.4% of 100%=0.554. That means the rest of the weight is MOF-5. MOF-5 weight percent=44.6%=0.446.

So, for 1 gram (g) of the composite there is 0.554 g TNM to 0.446 g of MOF-5.

Now take the oxygen balance of the individual components and multiply them by the weight of that component in the composite as follows: Since OB% of TNM =+49.0% and OB% of MOF-5 =-93.6%, the OB% of the composite is calculated as=(49.0×0.554)+(-93.6×0.446)=-14.6%

What is claimed is:
1. An energetic composition comprising:
   a first component comprising a nanostructured sorbent being a crystalline porous coordination polymer con- sisting of at least one metal node or cluster which is coordinated to an organic linker forming at least one porous framework; and a second component comprising an oxidant infiltrated into pores of the at least one porous framework of the nanostructured sorbent, wherein the second component is present in an amount such that the oxidant is at least 10% of the weight of the energetic composition;

a combination of the nanostructured sorbent and the oxidant resulting in the energetic composition material which is more sensitive to detonation by impact, friction, spark, or thermal stimulus than the oxidant alone.

2. The composition according to claim 1 where the ratio of oxidant to nanostructured sorbent is such that the value of the oxygen balance of the composition is closer to zero than the value of the oxygen balance of either of the components.

3. The composition according to claim 2 where the oxygen balance is less than 35% and more than −35%.

4. The composition according to claim 2 where the oxygen balance is less than 10% and more than −10%.

5. The composition according to claim 1 where the energetic composition has an impact sensitivity that is greater than that of pentaerythritol tetranitrate (PETN).

6. The composition according to claim 1 where the oxidizer is a liquid.

7. The composition according to claim 1 where the oxidizer is a solid.

8. The system according to claim 1 wherein said oxidant comprises tetranitromethane or hexanitroethane.

9. A method for producing the composition according to claim 1 comprising infiltrating the oxidant into pores of the porous network by diffusion in the vapor phase.

10. A method for producing the composition according to claim 1 comprising infiltrating the oxidant into pores of the porous network by melt infiltration.

11. A method for producing the composition according to claim 1 comprising infiltrating the oxidant into pores of the porous network by solution infiltration.

12. The composition according to claim 1 wherein the adsorption of oxidant into the nanostructured sorbent results in the energetic composition, which displays greater heat released upon decomposition than would be expected for decomposition of an equivalent quantity of the pure components.

13. The composition according to claim 1 wherein said organic linker is any carboxylate based organic molecule.

14. The composition according to claim 1 wherein said organic linker is any nitrogen-containing molecule.

15. The composition according to claim 1 wherein the at least one porous framework is a zeolitic imidazolate framework.

* * * * *

UNITED STATES PATENT AND TRADEMARK OFFICE
CERTIFICATE OF CORRECTION

PATENT NO. : 10,472,299 B2
APPLICATION NO. : 15/631519
DATED : November 12, 2019
INVENTOR(S) : Adam J. Matzger et al.

Page 1 of 1

It is certified that error appears in the above-identified patent and that said Letters Patent is hereby corrected as shown below:

In the Claims

At Column 21, Claim 1, Line 11, after "composition", delete "material".

At Column 22, Claim 8, Line 3, delete "system" and insert --composition--.

Signed and Sealed this
Thirty-first Day of March, 2020

Andrei Iancu
*Director of the United States Patent and Trademark Office*